(12) United States Patent
Diehr et al.

(10) Patent No.: US 9,329,135 B2
(45) Date of Patent: May 3, 2016

(54) MEANS FOR INSPECTING GLASS CONTAINERS FOR DEFECTS

(75) Inventors: Richard D. Diehr, Horseheads, NY (US); Amir R. Novini, Akron, OH (US); Richard A. Sones, Cleveland Heights, OH (US)

(73) Assignees: Emhart Glass S.A., Cham (CH); Applied Vision Corporation, Cuyaboga Falls, OH (US)

( * ) Notice: Subject to any disclaimer, the term of this patent is extended or adjusted under 35 U.S.C. 154(b) by 759 days.

(21) Appl. No.: 12/615,670

(22) Filed: Nov. 10, 2009

(65) Prior Publication Data

US 2010/0085426 A1 Apr. 8, 2010

Related U.S. Application Data

(62) Division of application No. 11/585,767, filed on Oct. 23, 2006, now Pat. No. 7,626,158.

(51) Int. Cl.
*G01N 21/90* (2006.01)
*B07C 5/34* (2006.01)

(52) U.S. Cl.
CPC .............. *G01N 21/90* (2013.01); *B07C 5/3408* (2013.01); *G01N 21/9054* (2013.01)

(58) Field of Classification Search
CPC .... B07C 5/3408; G01N 21/90; G01N 21/954; G01N 21/9054
USPC .......................... 250/223 B; 356/239.4, 240.1
See application file for complete search history.

(56) References Cited

U.S. PATENT DOCUMENTS

| | | | | |
|---|---|---|---|---|
| 4,488,648 A | * | 12/1984 | Claypool | 356/239.4 |
| 4,500,203 A | * | 2/1985 | Bieringer | 356/239.4 |
| 4,579,227 A | * | 4/1986 | Miller | 209/526 |
| 4,606,635 A | * | 8/1986 | Miyazawa et al. | 356/240.1 |
| 4,676,650 A | * | 6/1987 | Bjorndal et al. | 356/427 |
| 4,865,447 A | * | 9/1989 | Shay | 250/223 B |
| 4,915,237 A | | 4/1990 | Chang et al. | |
| 4,945,228 A | * | 7/1990 | Juvinall et al. | 250/223 B |
| 5,020,908 A | * | 6/1991 | Hermann | 356/239.1 |
| 5,305,391 A | | 4/1994 | Gomibuchi | |
| 5,486,692 A | | 1/1996 | Baldwin | |
| 5,608,516 A | * | 3/1997 | Emery | 356/239.4 |
| 5,617,204 A | * | 4/1997 | Hinata | 356/239.4 |
| 5,719,679 A | | 2/1998 | Shimizu et al. | |
| 5,729,340 A | | 3/1998 | Griesbeck et al. | |
| 5,895,911 A | | 4/1999 | Giometti et al. | |
| 5,900,945 A | * | 5/1999 | Hinata et al. | 356/240.1 |
| 6,025,909 A | | 2/2000 | Juvinall et al. | |
| 6,031,221 A | | 2/2000 | Furnas | |
| 6,104,482 A | * | 8/2000 | Brower et al. | 356/239.4 |
| 6,211,952 B1 | * | 4/2001 | Weiland et al. | 356/239.4 |
| 6,275,287 B1 | | 8/2001 | Watanabe | |
| 2003/0035103 A1 | * | 2/2003 | Werzinger et al. | 356/239.1 |
| 2005/0174571 A1 | * | 8/2005 | Cochran et al. | 356/240.1 |
| 2006/0000968 A1 | * | 1/2006 | Katayama et al. | 250/223 B |
| 2011/0216187 A1 | * | 9/2011 | Bocker | G01N 21/9036 348/127 |

FOREIGN PATENT DOCUMENTS

| EP | 0497477 | 8/1992 |
|---|---|---|
| JP | 02257044 | 10/1990 |

* cited by examiner

*Primary Examiner* — Georgia Y Epps
*Assistant Examiner* — Kevin Wyatt
(74) *Attorney, Agent, or Firm* — Reinhart Boerner Van Deuren s.c.

(57) ABSTRACT

A machine for inspecting a rotating glass container for defects wherein the image evaluated for defects is a critical addition of a plurality of additions each defined by a plurality of time spaced images.

15 Claims, 8 Drawing Sheets

MEANS FOR INSPECTING GLASS CONTAINERS FOR DEFECTS

CROSS REFERENCE TO RELATED APPLICATIONS

This patent application is a division of U.S. patent application Ser. No. 11/585,767, filed on Oct. 23, 2006 now U.S. Pat. No. 7,626,158, entitled "Machine For Inspecting Glass Containers," which patent application is assigned to the assignee of the present invention, and which patent application is hereby incorporated herein by reference in its entirety.

BACKGROUND OF THE INVENTION

Field of the Invention

The present invention relates to machines, which inspect glass containers for defects, and more particularly, to a system which inspects for cracks in translucent glass containers.

In the glass container industry, small cracks or fracture in the glass are referred to as "check defects." Checks can range from sub millimeters to several hundred millimeters and can be oriented at any direction from vertical to horizontal. Glass is not a crystalline structure by nature, but most cracks propagate roughly along a plane of some orientation in space mostly determined by the shape of the glass at that location. For example, a crack that began as a vertical crack at the upper surface of the mouth primarily propagates in a vertical plane. Checks can appear in any orientation and on any portion of a container and can exist wholly within the glass or may penetrate to one or both surfaces. Checks are considered phase objects and do not absorb light like a solid object does. Checks are primarily reflective in nature if their opposed surface separation is at least half a wavelength of light. However, very few checks with a smaller separation will reflect light and accordingly they will not likely be detectable by direct reflection methods, but they might have scattering points when they penetrate to the one or both surfaces of the container and will scatter light back to the sensors.

Most of these crack defects will drastically weaken the bottle, often causing it to rupture or to leak. Therefore, bottle manufactures like to remove these containers before they reach filing plants. Checks appearing near the mouth of the containers are called finish checks. In the glass bottle industry, the term "container finish" refers to the portion of the bottle that defines the mouth, threads or beads, and the ring. The upper surface of the mouth is referred as the sealing surface.

Almost all commercially available check detectors work on the principle of reflected light. A conventional check detector consists of a series of continuously operating light spot light sources and associated photodetectors that are positioned so that known checks on a bottle rotating at an inspection station will reflect light from one of the sources to one of the photo-detectors. Signal processing of the photodetector outputs recovers the sharp peaks while rejecting lower frequency signal variations caused by ambient light, reflection from the bottle sidewall, etc.

While commercially available check detectors are successfully deployed on most glass bottle production lines, there are several drawbacks to the approach. A few of those are: many point sensors are required for many possible reflection angles; some sensor angles are difficult to position; additional sensors and lights need to be added as more production defects appear; time consuming setup is required for each type of container; and the difficulty of reproducing the same setup from one inspection line to another.

The following U.S. Pat. Nos. 4,701,612, 4,945,228, 4,958,223, 5,020,908, 5,200,801, 5,895,911, 6,104,482, 6,211,952, and 6,275,287 all relate to devices that detect defects in the finish of a container.

It is an object of the present invention to provide an apparatus for inspecting glass containers, which can detect vertical, horizontal, and any other angle cracks on a bottle which is user friendly and easily adjusted. Another object of this invention is to provide a detector that can detect known types of checks and also any new checks without specific setup requirements.

Other objects and advantages of the present portion of this invention will become apparent from the following accompanying drawings which illustrate, in accordance with the mandate of the patent statutes, a presently preferred embodiment incorporating the principles of the invention.

OBJECT OF THE INVENTION

It is an object of the present invention to provide an apparatus for inspecting glass containers, which can detect vertical, horizontal, and any other angle cracks on a bottle which is user friendly and easily adjusted. Another object of this invention is to provide a detector that can detect know types of checks and also any new checks without specific setup requirements.

Other objects and advantages of the present portion of this invention will be come apparent from the following accompanying drawings which illustrate, in accordance with the mandate of the patent statues, a presently preferred embodiment incorporating the principles of the invention.

BRIEF DESCRIPTION OF THE DRAWINGS

These and other objectives and advantages will become readily apparent from the following written description of embodiments of the invention and from the drawings in which.

DETAILED DESCRIPTION OF THE EXEMPLARY EMBODIMENTS

Figure 1:
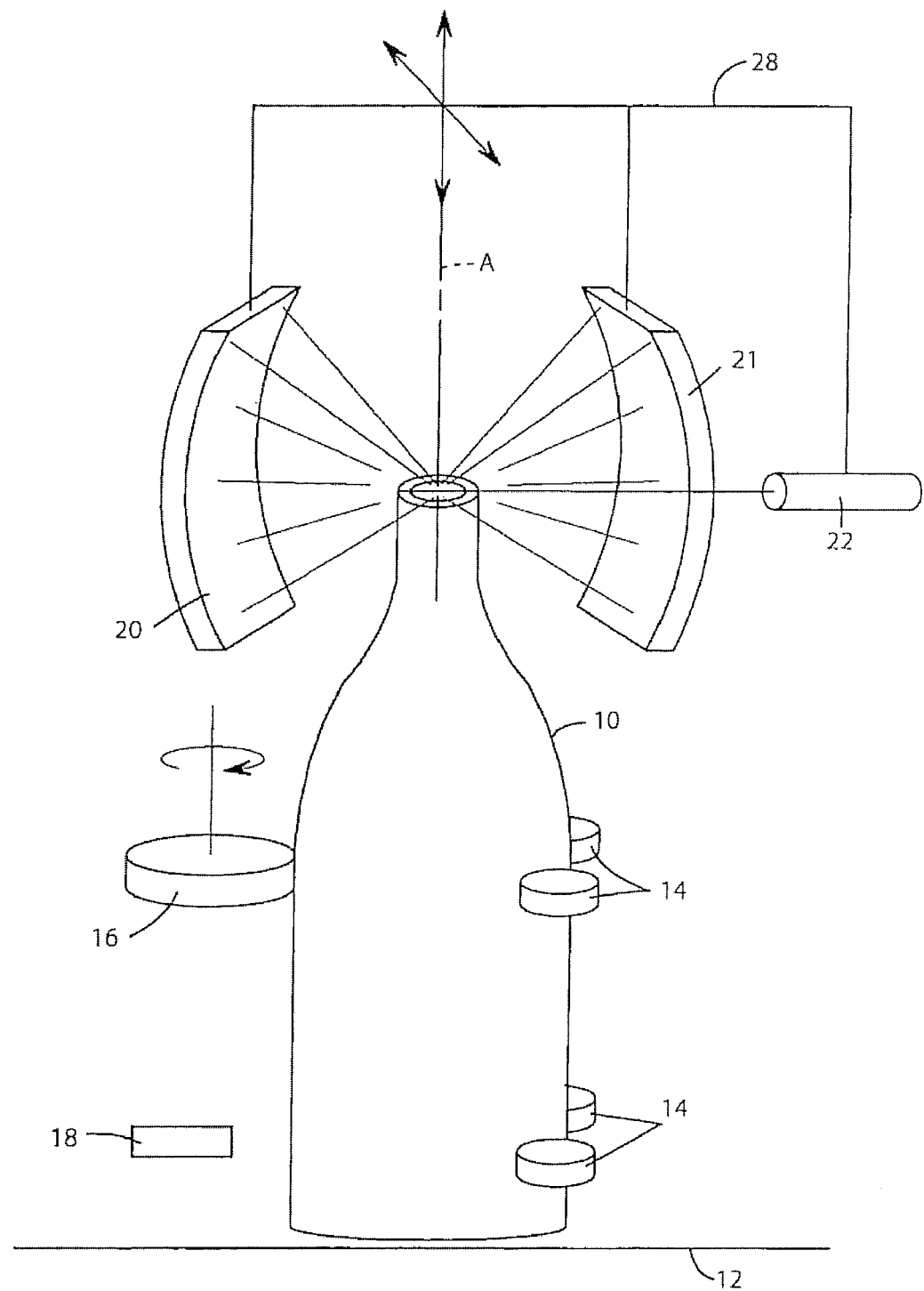
FIG. 1 is an oblique elevational schematic view of an inspection station of a machine for inspecting glass containers for checks and other defects, made in accordance with the teachings of the present invention.

In a machine for inspecting glass containers (bottles), the containers 10 are transported along a conveyor 12 to an inspection station illustrated in FIG. 1. The conveyor may be a linear belt or a turret type feed system. A container 10 is engaged by upper and lower rear pairs of idler rollers 14 and a front drive wheel 16 so that rotation of the drive wheel in the clockwise direction will rotate the container in the counter-clockwise direction. There is conveyor dwell of sufficient duration at the inspection machine so that the container can be rotated more than 360 degrees while the inspection takes place. A container present sensor 18 will sense the presence of a container at the inspection station (the sensor can be upstream and the actual presence of the container at the inspection station could be defined by an encoder count following the sensing of the container by the upstream part present sensor. Light sources (Light Source #1/20 (see FIGS. 1 and 2) and Light Source #2/21) illuminate the finish portion of the container and a Camera/22 images the finish portion.

Figure 2:
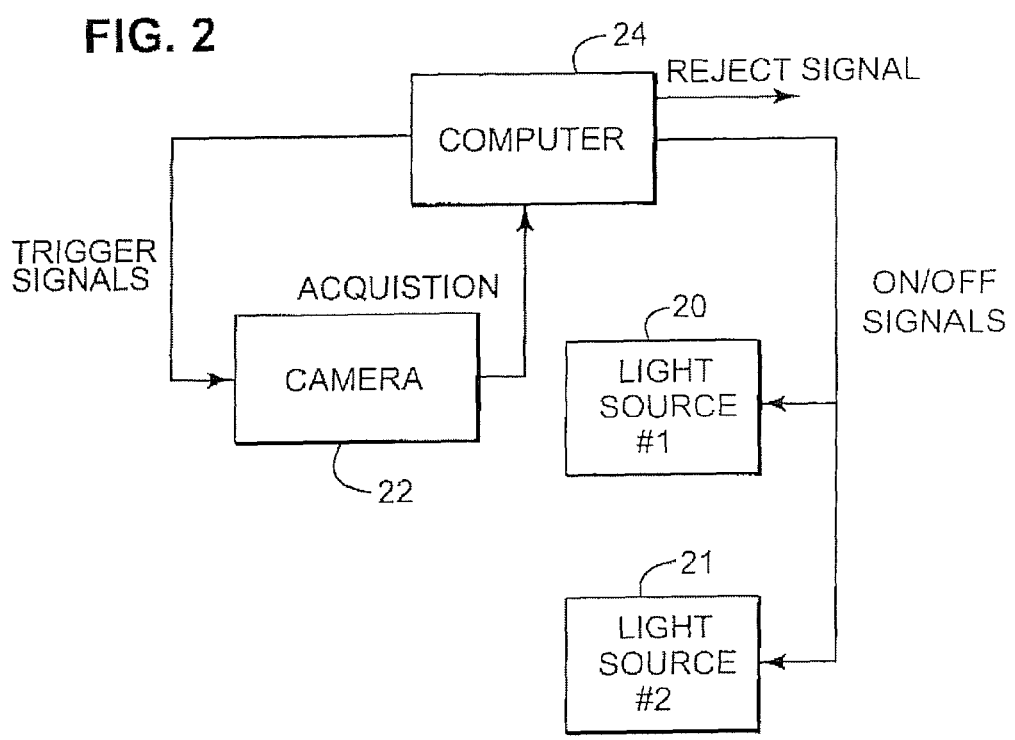
FIG. 2 is a block diagram showing the operation of the pairs of light sources and camera shown in FIG. 1.

FIG. 2 illustrates the operation of the Camera and Light Sources. A Computer 24 delivers On/Off signals to Light Source #1/20 and Light Source #2/21 and delivers Camera Trigger signals to the Camera/22. The Camera has a matrix array of elements (pixels) to receive an image of the finish portion of the container during the Camera's exposure period. The Camera could be a CCD, MOS or like camera which will store an image until the next Trigger Signal. When a Trigger Signal is received, the existing image will be captured and transferred, as an "Acquisition," to the Computer so that it can be recorded and processed by the Computer. The Computer will issue a Reject Signal if a defect is identified.

Figure 3:
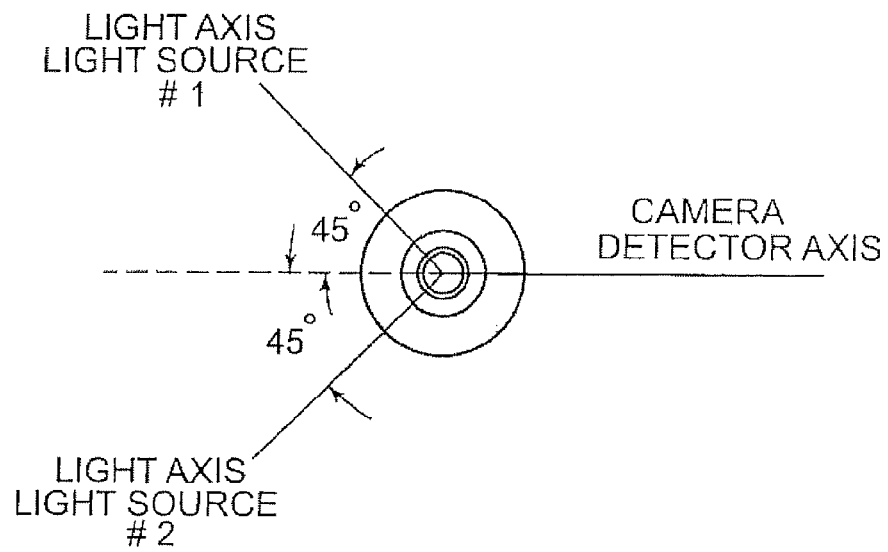
FIG. 3 is a schematic top view of the container at the inspection station showing the light axes of a pair of light sources and the camera.
Figure 4:
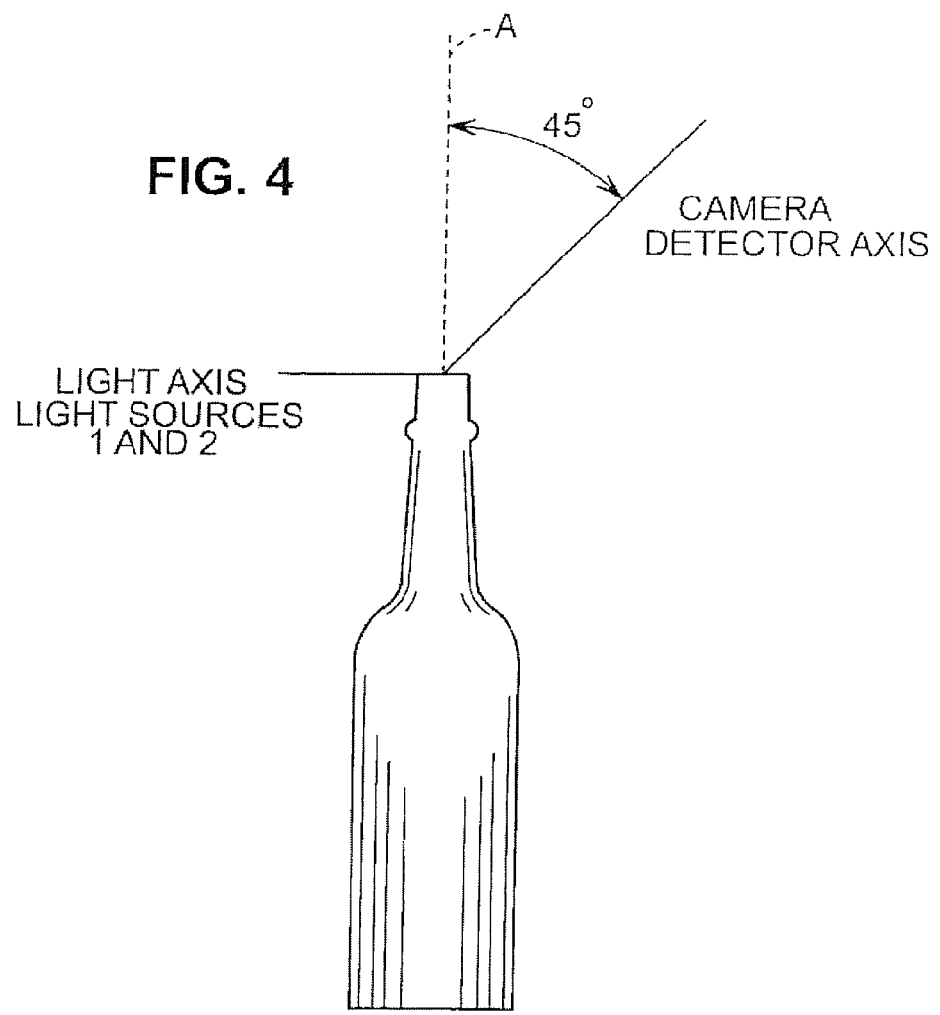
FIG. 4 is a schematic elevational view showing the light axes of the light sources and camera shown in FIG. 3.
Figure 5:
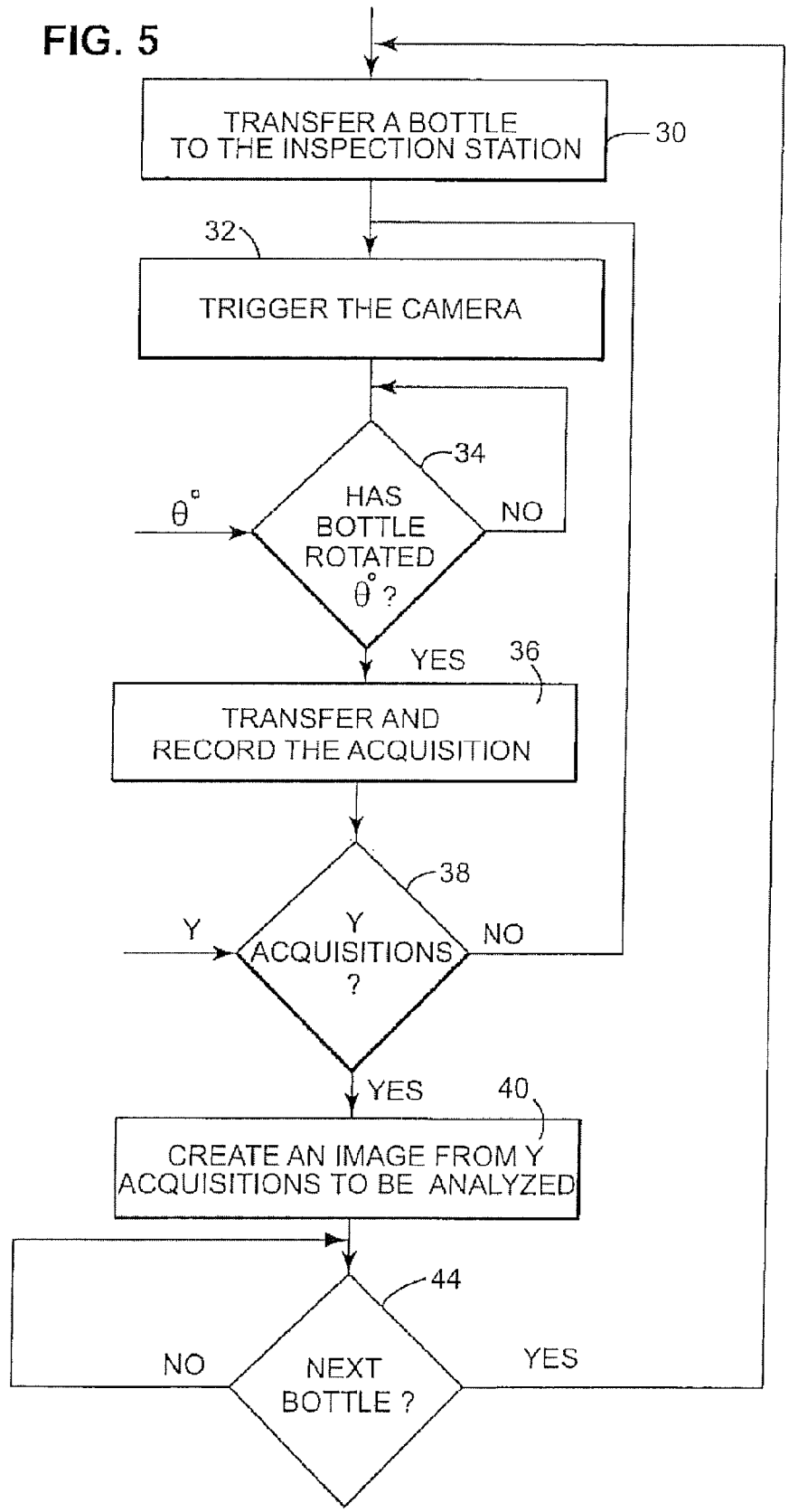
FIG. 5 is a logic diagram illustrating the operation of the camera system of the inspection machine.

As can be seen from FIGS. 3 and 4, the Light Axis for each light source, which is in the positive "Z" plane of the container, is horizontal and intersects the axis "A" of the container. The two light axes are orthogonal to each other and 45° to a vertical plane including the Camera Detector Axis. The Detector Axis for the Camera/22, which is located in the negative "Z" plane, is approximately 45° from horizontal. With this relationship, the camera is looking at a dark field and seeing only light coming from the checks. The light sources and camera are supported by structure 28 that can be vertically displaced and horizontally displaced to reposition the system for different height/diameter containers.

To start an inspection, the machine will Transfer A Bottle To The Inspection Station/30. Following a time sufficient for the rotation of the bottle, by the drive wheel, to become stable, the Computer will Trigger The Camera/32. This starts the acquisition of the image. The following explanation is provided in terms of angles for purposes of clarity, but it should be understood that in a digitally controlled camera, instructions may be time based rather than defining actual angles so that when something is to occur in an approximate $\theta°$ ($60°$ angle in the preferred embodiment), an approximate time (number of pulses) may be selected which approximately corresponds to that angle and where events are desired approximately every 7.5°, for example, the pulses could be divided by 8. When the query "Has Bottle Rotated $\theta°$?"/34 ($\theta°$ or a selected number of pulses corresponding approximately to that angle of rotation can be set) is answered in the affirmative, the Computer will Transfer And Record The Acquisition/36. Once the Camera is triggered, the Camera will capture data until the Camera is again triggered (following the rotation through $\theta°$). When the Computer answers the query "Y Acquisitions?" in the negative, the Computer will again Trigger The Camera/32. When the computer answers the query "Y Acquisitions?"/38 in the affirmative ("Y" may be set and is six in the preferred embodiment), the Computer will Create An Image From Y Acquisitions To be Analyzed/40. The image created (a Critical Addition), where as in the preferred embodiment "Y" is six, will represent the entire (approximately) 360° surface of the finish and will be the Critical Addition of six acquisitions each imaging eight illuminations.

The critical addition will be made in a manner that will maximize the data that indicates that a defect is present. The Critical Addition can represent for each pixel location, the highest intensity of the corresponding pixel in all six Acquisitions which will make up the Critical Addition. Then, when the Computer answers the inquiry Next Bottle?/44 in the affirmative, the next bottle can be processed.

An image processing technique may be used to enhance the signal created by checks from signal created by mold features of the container. First, a reference or "mask image", can be created using a set of sample containers without defects running through the inspection setup (containers without defects are referred as "good ware" and containers with defects that need to be removed during the inspection as "bad ware"). To incorporate all the signals created by good ware from different molds that may contain slightly different structural variations, and small variations of signals due to vibrations and rotation, a large number of images can be acquired and processed to create the mask image. These images contain almost all the possible variation of light reflection by mold marks, threads, seams, and curved surface of good ware. Mask image is created by combining all the good ware images. A mask image is created and is compared with the reference mask created with good ware. The difference between the image and the mask shows the signals created by check defects.

Figure 6:
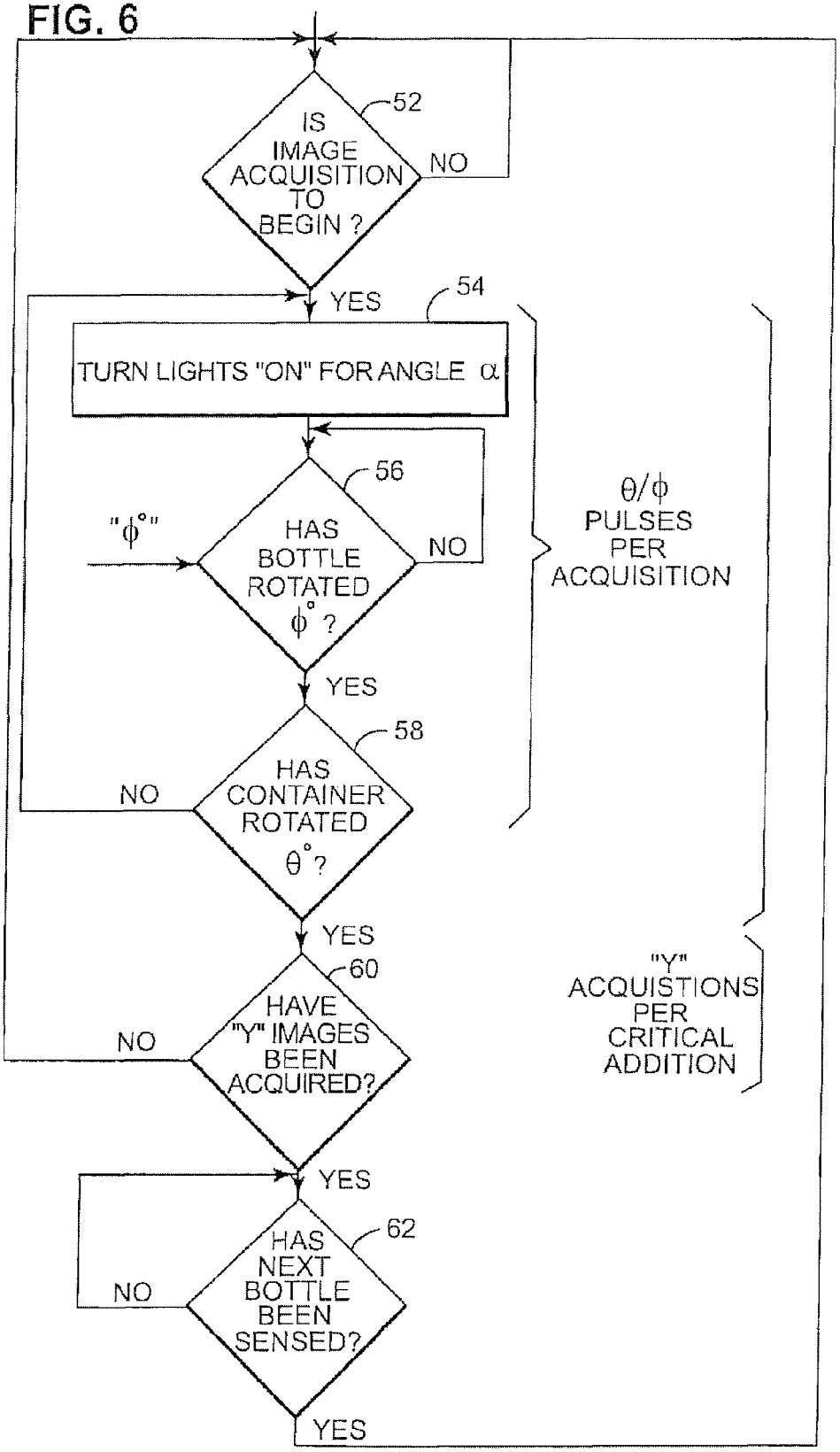
FIG. 6 is a logic diagram illustrating the operation of the lighting system of the inspection machine.

FIG. 6 illustrates the operation of the light sources. When the Computer answers the query "Is Image Acquisition To Begin?"/52 in the affirmative, the Computer will Turn Lights "On" For Angle "$\alpha$°"/54 ("$\alpha$" may be set and could be a defined number of pulses). When the Computer answers the query "Has Container Rotated "$\Phi$°"/56 in the affirmative ($\Phi$ can be set), and answers the query "Has Container Rotated $\theta°$?"/58 in the negative, the light sources will again be turned "on". When this inquiry is answered in the affirmative ($\theta/\Phi$ pulse per acquisition), and the query "Have "Y" Images Been Acquired?/60", in the negative the entire surface has not been imaged and the entire process can be repeated until "Y" images have been acquired (Y pulses per acquisition). Then, when the computer answers the inquiry "Has Next Container Been Sensed?"/62 in the affirmative, the entire process can be repeated for the next bottle. If the lights are to be on for the entire time that the camera is triggered ($\alpha$ can be set to equal $\theta°$).

To reduce noise, $\alpha$ is, in the preferred embodiment, defined so that the surface will be illuminated a small portion (25%) of the angle $\Phi$°. Checks that will cause a container to be rejected have been found to be imaged when the light sources are "on" only a small fraction of $\alpha$. This fraction can be empirically varied to achieve a desired result. While the imaging process has been disclosed with reference to checks in the finish area of the container, it can be used to identify body or heel checks and other defects.

Figure 7:
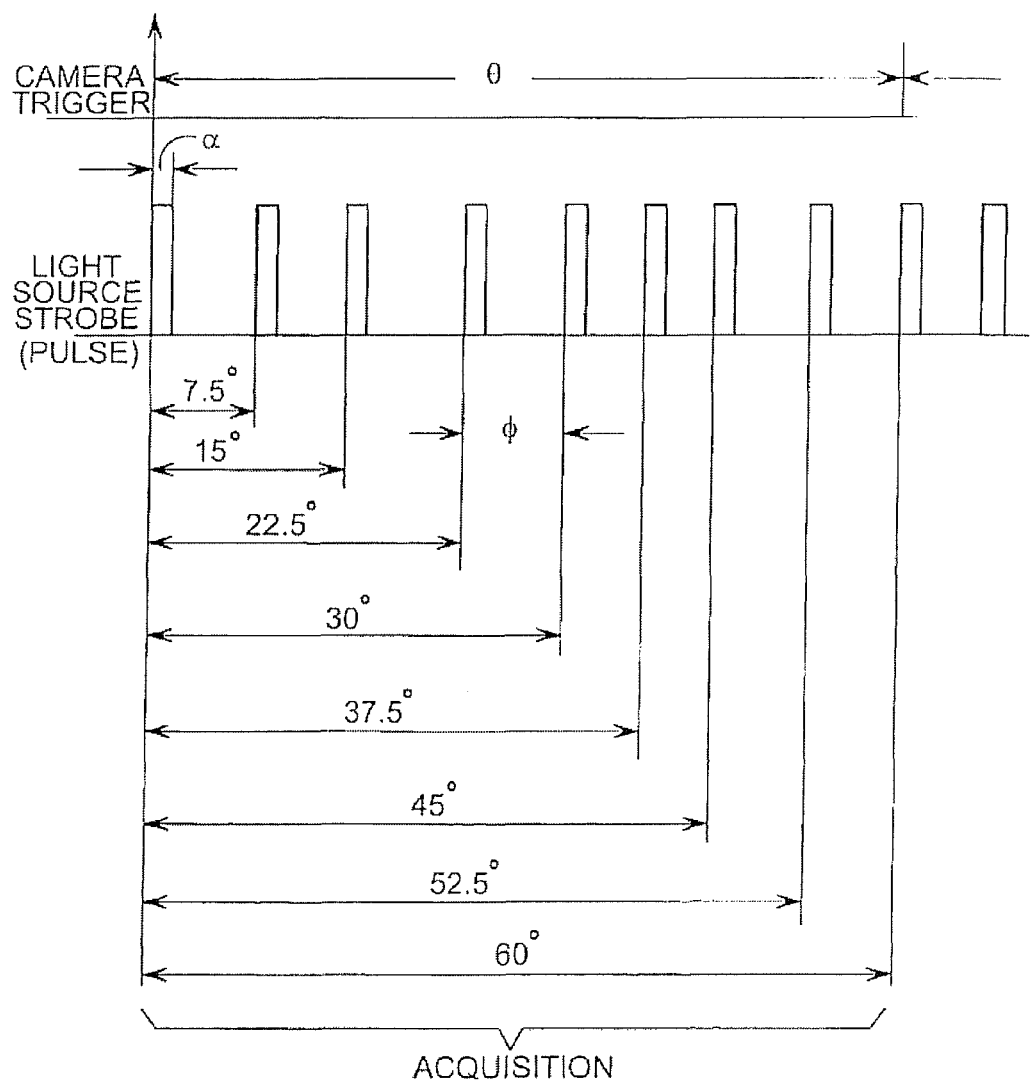
FIG. 7 is a timing diagram illustrating the operation of the light sources.

FIG. 7 is a timing diagram for an Acquisition comprised of light sources turned on $\alpha$ degrees for every $\Phi$° (7.5° in the preferred embodiment) through $\theta°$ (60° in the preferred embodiment). The lower the ratio of $\alpha/\Phi°$, the less noise will be available to interfere with the desired signal.

Figure 8:
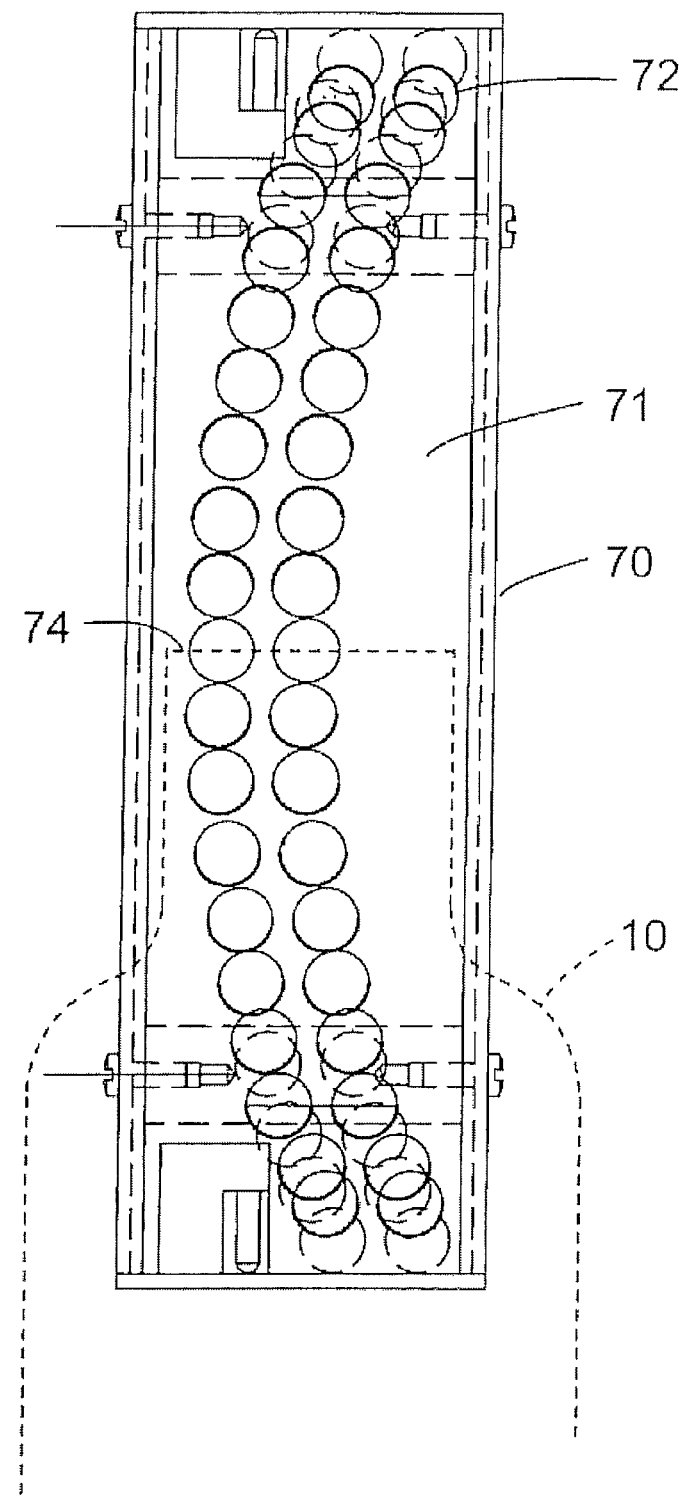
FIG. 8 is a side elevational view of one of the light sources.
Figure 9:
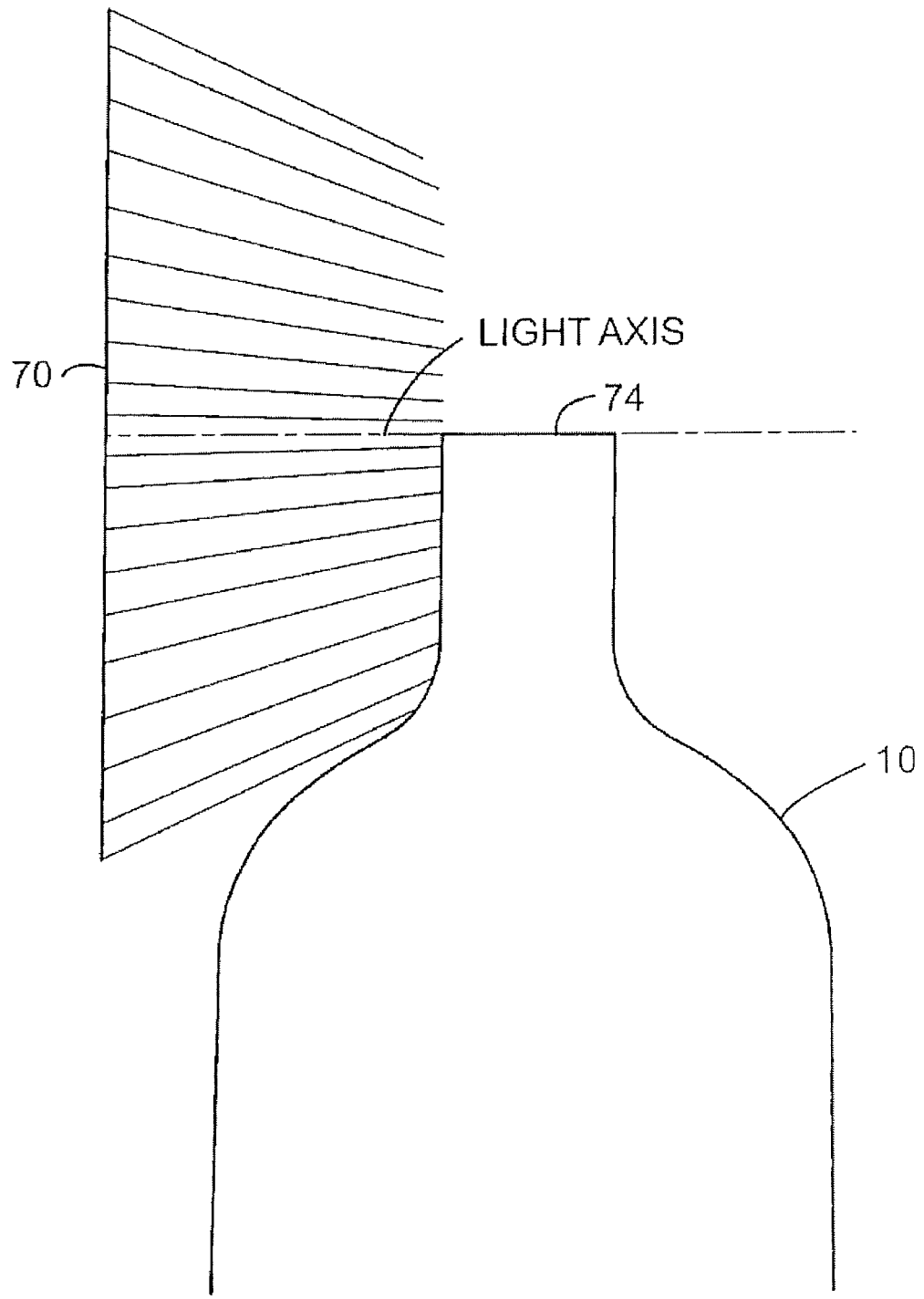
FIG. 9 is an elevational view showing how the LED's of one of the light sources are aimed toward the finish.

The light sources 70 (FIGS. 8 and 9) are mirror images and are segments of an arc. As shown the light source, mounted on a flat panel 71, is perpendicular to the Light Axis and faces the finish of the container 10 which is shown in dotted lines. The segment has inner and outer (or three or four, . . . ) rows of LED's 72 with the central LED's 74, which define the Light Axis, standing parallel to the Light Axis and with the remaining LED's being progressively tilted toward the light axis as they proceed away from the Light Axis. The preferred location of the Light Axis is at the sealing surface 74 but it can be located from the sealing surface to the bottom of the finish. The ideal geometry that the preferred embodiment attempts to approach is that of conical illumination, where the top and bottom of the cone are dark so that the camera will not see any direct reflections of light. Viewing the finish as a torus, this conical geometry allows the maximum light to be projected onto the finish with direct reflection. Only an anomaly in the finish (a check) will generate direct reflections to the camera.

This apparatus has following advantages: because the area sensor image an area of the bottle, it is possible to detect almost all the checks in that region. This makes the inspection independent of the specific orientation and location of the check, and thus enable detecting "new" checks without changing the setup. The positioning of the area array sensors and light sources would not depend essentially on the geometry of the bottle. It will be easier to setup for most of the containers with little or no adjustments.

Although the foregoing description of the present invention has been shown and described with reference to particular embodiments and applications thereof, it has been presented for purposes of illustration and description and is not intended to be exhaustive or to limit the invention to the particular embodiments and applications disclosed. It will be apparent to those having ordinary skill in the art that a number of changes, modifications, variations, or alterations to the invention as described herein may be made, none of which depart from the spirit or scope of the present invention. The particular embodiments and applications were chosen and described to provide the best illustration of the principles of the invention and its practical application to thereby enable one of ordinary skill in the art to utilize the invention in various embodiments and with various modifications as are suited to the particular use contemplated. All such changes, modifications, variations, and alterations should therefore be seen as being within the scope of the present invention as determined by the appended claims when interpreted in accordance with the breadth to which they are fairly, legally, and equitably entitled.

What is claimed is:

1. An apparatus for detecting a check in a glass container, the glass container including a sealing surface and a glass container axis, the apparatus comprising:
    a container rotation device configured to rotate the glass container more than 360 degrees about the glass container axis;
    a light source configured to project light toward the glass container non-parallel with the glass container axis to illuminate a selected portion of the glass container, with at least a portion of the light source aligned in a horizontal plane with the selected portion of the glass container, the horizontal plane being orthogonal with the glass container axis; and
    a camera aligned for imaging the selected portion of there glass container, wherein the check is detected by the camera from a combination of a plurality of consecutive images of the selected portion of the glass container image reflections of the check on the glass container that are illuminated by the light source;
    a computer configured to trigger the camera to acquire a plurality of acquisitions, to cause the light source to illuminate at least a portion of the glass container for a period of time during each acquisition, and to create a critical addition from the plurality of acquisitions;
wherein the camera and the light source are configured relative to one another such that when the selected portion does not include a check, the camera views a dark field and when the selected portion includes a check, the camera views light reflected from the check.

2. The apparatus of claim 1, wherein the light source is composed of a plurality of LEDs aligned in a vertically extending array spaced apart from and parallel to the glass container axis as an arc, with one of the LED positioned at the center of the arc defining a light axis.

3. The apparatus of claim 2, including at least one additional row of LEDs aligned as an arc and positioned a distance from the other row of LEDs.

4. The apparatus of claim 2, wherein the light axis is aligned with the sealing surface of the glass container.

5. The apparatus of claim 1, wherein the container rotation device includes a drive wheel and a plurality of idler wheels.

6. The apparatus of claim 1, including a conveyor configured to move the glass container to an inspection station.

7. The apparatus of claim 1, wherein the light source includes a first light source and a second light source configured to illuminate the selected portion of the glass container, with at least a portion of the second light source aligned with the selected portion.

8. The apparatus of claim 7, wherein the second light source is positioned radially ninety degrees from the other light source with the camera positioned along an axis radially one hundred and thirty-five degrees from each of the two light sources.

9. The apparatus of claim 8, wherein the two light sources are configured to provide a conical illumination of the selected portion of the glass container for maximum light projection onto the glass container finish.

10. A method for detecting an anomaly in a glass container, the glass container including a sealing surface and having a glass container axis, the method comprising:
    moving the glass container to an inspection station;
    rotating the glass container about the glass container axis at the inspection station;
    positioning a first light source to selectively illuminate a selected portion of the glass container, the first light source defining a light axis that intersects the glass container axis;
    positioning a camera to image the selected portion of the glass container with the camera obtaining a plurality of images, each image taken as the container is rotated over a selected angular distance;
    turning the first light source on and off a plurality of times as the container is rotated over the selected angular distance;
wherein the first light source and the camera are configured such that the camera will image a dark field when the selected portion does not include an anomaly and the camera will image light reflected from an anomaly when the selected portion does include an anomaly; and,
    detecting an anomaly from a critical addition created using the plurality of images of the glass container, the images indicating a reflection of light from the light source reflected from an anomaly of the glass container if the container includes an anomaly.

11. The method of claim 10, including the step of positioning a second light source radially ninety degrees from the first light source, with the camera positioned along an axis radially forty-five degrees from each of the first and second light sources.

12. The method of claim 10, including the step of configuring the two light sources to provide a conical illumination of the selected portion of the glass container for maximum light projection onto the glass container finish.

13. The method of claim 10, including rotating the glass container more than 360 degrees.

14. The method of claim 10, wherein the light source is composed of a plurality of LEDs aligned as an arc on a flat panel, the flat panel being substantially parallel with the glass container axis, with one of the LEDs positioned at the center of the arc.

15. The method of claim 13, wherein the light axis is aligned with the sealing surface of the glass container.

* * * * *